United States Patent [19]

Jansen

[11] Patent Number: 4,887,472

[45] Date of Patent: Dec. 19, 1989

[54] SAMPLER

[75] Inventor: Adolf E. Jansen, Rotterdam, Netherlands

[73] Assignee: Douwes Vastgoed B.V., Rotterdam, Netherlands

[21] Appl. No.: 275,076

[22] Filed: Nov. 22, 1988

[30] Foreign Application Priority Data

Dec. 2, 1987 [NL] Netherlands .................. 87 02896

[51] Int. Cl.$^4$ ............................................. G01N 1/00
[52] U.S. Cl. ................................................. 73/863.86
[58] Field of Search ........... 73/863.72, 863.81, 863.85, 73/863.86, 864.22, 864.33, 864.51, 864.63, 864.73, 864.74, 863.86

[56] References Cited

U.S. PATENT DOCUMENTS

| | | | |
|---|---|---|---|
| 1,534,939 | 4/1925 | Fuge .................................. | 73/864.51 |
| 3,719,086 | 3/1973 | Bannister et al. ................ | 73/864.22 |
| 3,776,042 | 12/1973 | Werra et al. ..................... | 73/863.85 |
| 4,174,632 | 11/1979 | Jansen ............................... | 73/863.86 |
| 4,252,021 | 2/1981 | Drushel ............................. | 73/863.86 |
| 4,580,452 | 4/1986 | Masson ............................. | 73/863.86 |
| 4,651,574 | 3/1987 | Spencer ............................ | 73/863.86 |

FOREIGN PATENT DOCUMENTS

| | | | |
|---|---|---|---|
| 2752284 | 6/1978 | Fed. Rep. of Germany ... | 73/863.86 |
| 2907558 | 8/1980 | Fed. Rep. of Germany ... | 73/863.85 |
| 0549706 | 3/1977 | U.S.S.R. ............................ | 73/863.86 |

Primary Examiner—Robert R. Raevis
Attorney, Agent, or Firm—Richard C. Woodbridge

[57] ABSTRACT

A sampler including a hood having a valve mounted at one end and a reciprocally related sleeve slidably mounted in the hood. a sample bottle having a septum is held in a bottle retainer that is slidably mounted on the hood. A pair of needles extend from the hood and communicate with a pair of bores that extend through the hood. One bore is vented to the exterior while the other bore communicates with channels in the valve. The needles may be sterilized, in a simple manner, prior to and/or after sampling. In a special embodiment of the sampler it is possible to sterilize the needles after sampling and before the needles contact the ambient air.

14 Claims, 4 Drawing Sheets

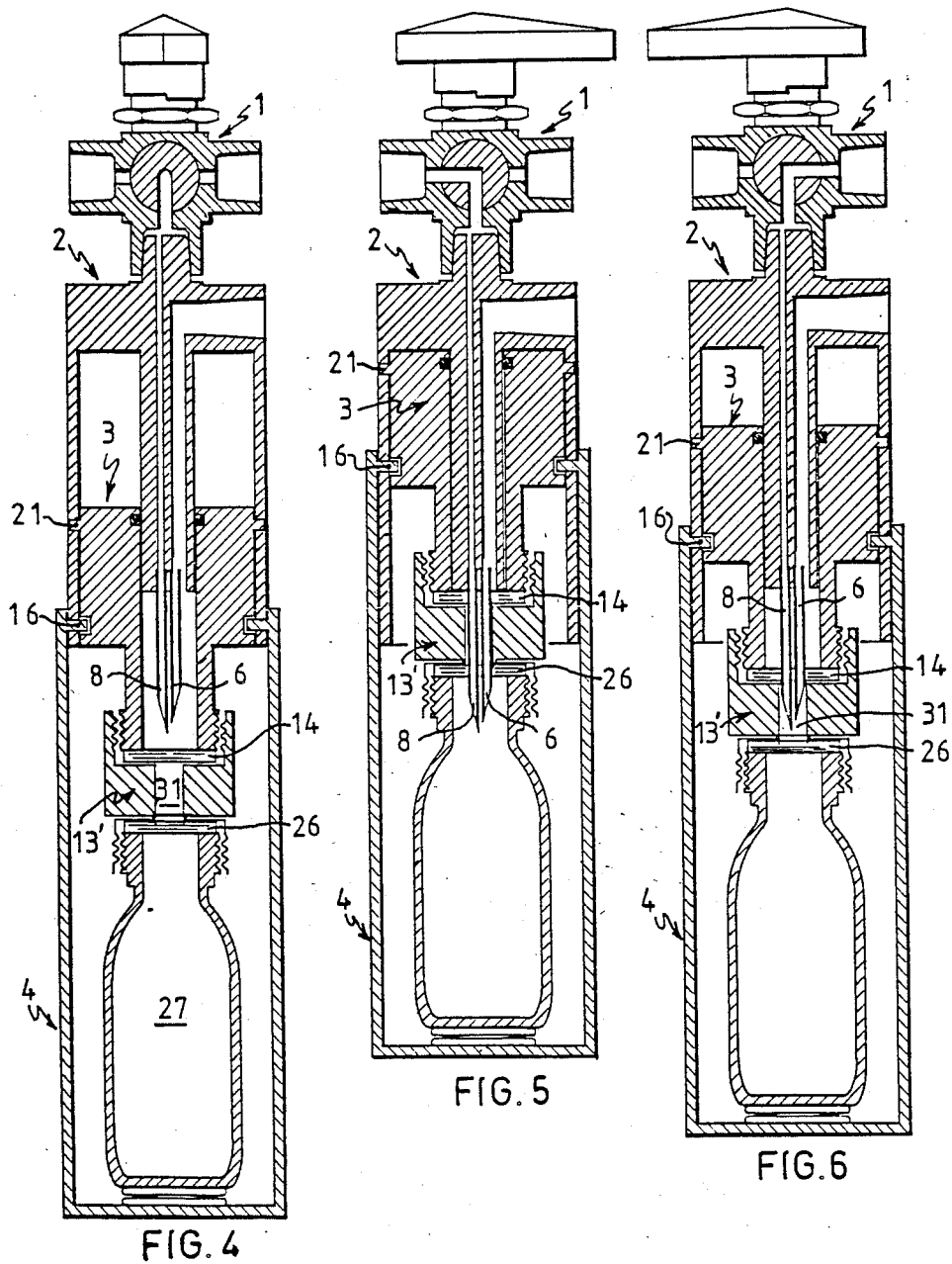

SAMPLER

BACKGROUND OF THE INVENTION

1. Field of the Invention

The invention relates to a sampler comprising a multi-way valve that is connected to a hood comprising at least one needle that can pierce a septum of a sample bottle.

2. Description of Related Art

A similar sampler is known from Dutch patent application No. 77 07477 by Applicant, on which Dutch patent 173558 was granted. In this known sampler it is not possible in a simple manner to sterilize the needle prior to and/or after sampling by means of steam or a liquid, before the needle or needles come into contact with the ambient air.

SUMMARY OF THE INVENTION

The invention aims to improve the above. According to the present invention, this has been attained in that within the hood a sleeve, reciprocable by a bottle, has been arranged that can be sealed by means of a septum at the end facing away from the the valve, so that both septums are pierced during the sleeve's motion in the direction of the valve, or at lest the one needle withdraws from the two septums during the sleeve's motion away from the valve, respectively, so that the needle can be rinsed with another medium directly before or after sampling.

Of course it is also possible to sterilize without having a septum on the sleeve, but then the sample bottle cannot be removed right after sampling, which means a loss of time. Moreover, the septum and the sample could be affected by the high temperatures if steam is used.

The hood can have stub projecting in the centre over which the sleeve can slide by the interposition of a packing.

An axial slit may have been made in the hood for receiving an outwardly directed projection of the sleeve, which projection is devised to allow the sleeve to reciprocate only rectilinearly in the sleeve.

Thus it is important for the invention that the bottle and sleeve can be interconnected in some way. In principle, this could be done by means of a coupling sleeve that connects the two septums. This embodiment, however, has not been further elaborated.

In a possible embodiment the slit of the hood at the end of the sleeve facing away from the valve merges into an S-curve, forming a bayonet fit together with the substantially perpendicular slit in the sleeve for an inwardly projection for a bottle retainer suspended from the hood. The slit may also have a branch near the end facing towards the valve, which branch forms a bayonet fit for a bottle retainer moved towards the operation position.

The bottle retainer may comprise a spring means that firmly pushes the septum or a sample bottle against the septum of the sleeve when the projection of the sleeve has reached the end of the slit.

If the bent portion of the substantially perpendicular slit of the sleeve extends obliquely upwardly, its end being aligned with the end of the branch of the hood, the septums are pushed together even more firmly.

The bottle retainer preferably also comprises centering means for the sample bottle. The bottle retainer may also comprise a checking slit, applied in the known manner, in order to check the contents of the bottle.

If the sampler is fitted with a long supply needle and a short vent needle, the vent needle may have been mounted with the aid of a ring in a relatively wide vent bore of the hood.

The septum of the sleeve is preferably mounted on the sleeve by means of a screw cap comprising a hole. This combination of screw cap and septum can be replaced by a closed cap so as to allow rinsing by means of another medium without a septum being present, to be performed.

It is also possible that the septum of the sleeve is mounted on the sleeve by a screw head comprising a chamber that comprises at its side facing away from the septum a sharp edge.

BRIEF DESCRIPTION OF THE DRAWINGS

The invention will be further elucidated hereafter on the basis of the drawing, showing by means of example a number of embodiments of a sampler according to the invention. In the drawing, respectively.

DETAILED DESCRIPTION

Figure 1:
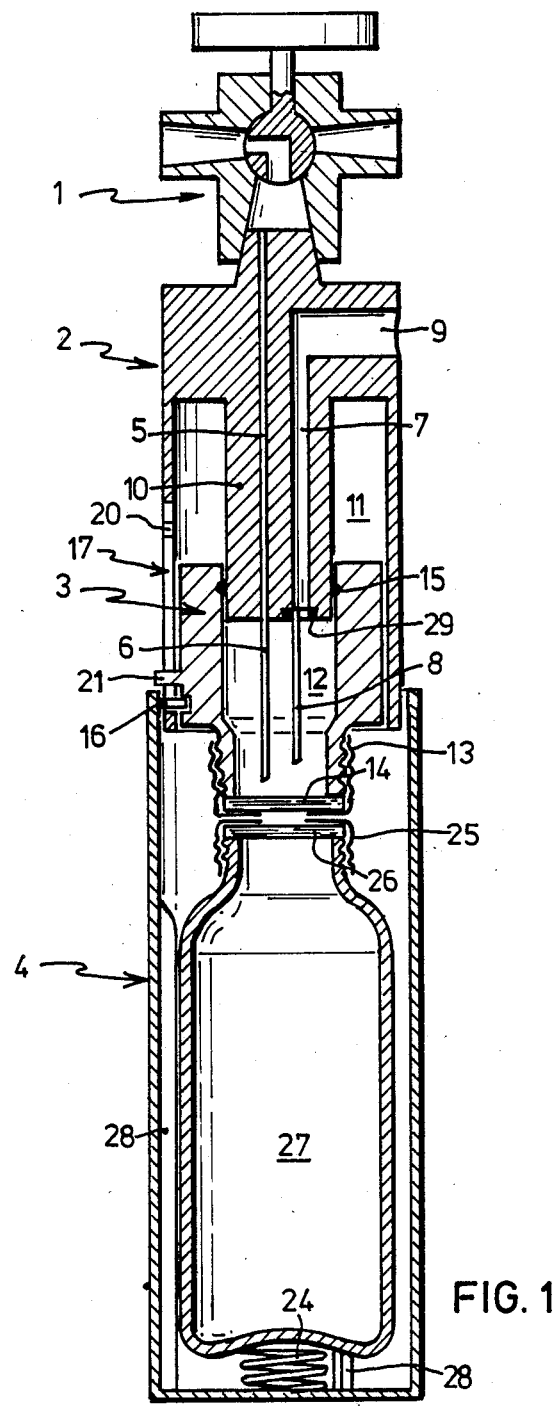
FIG. 1 shows a schematic, vertical section of a first embodiment of a sampler.
Figure 2:
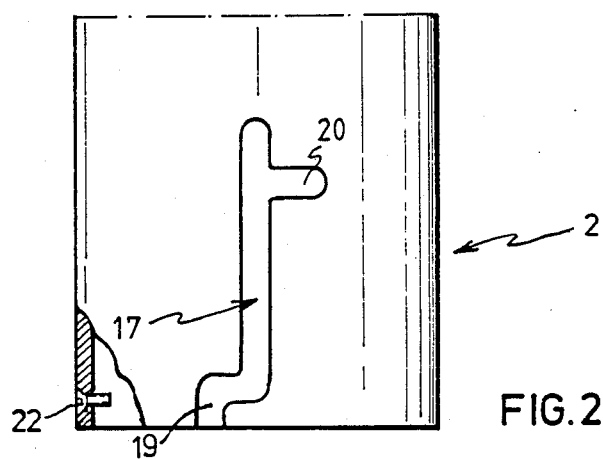
FIG. 2 shows a view of the hood of the sampler of FIG. 1, rotated over 90° with respect thereto.
Figure 3:
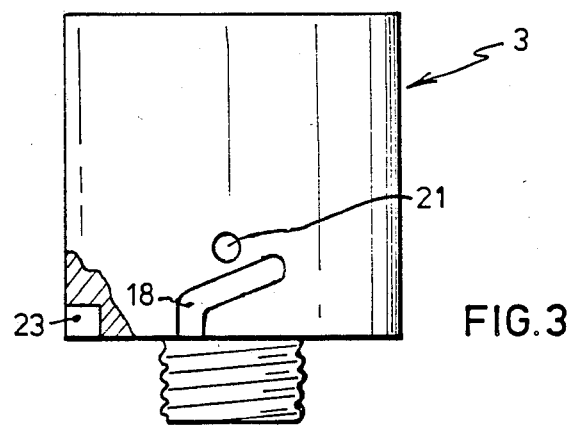
FIG. 3 shows a view of the sleeve of the sampler, also rotated over 90° with respect to FIG. 1, FIGS. 4-6 show three positions of a second embodiment of the sampler.
Figure 7:
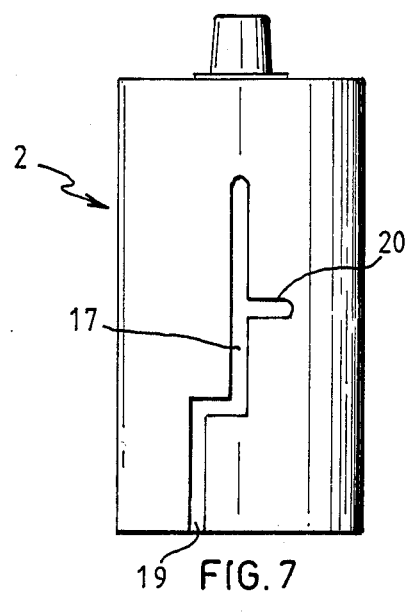
FIG. 7 shows a view of the head of the sampler of FIGS. 4-6.
Figure 8:
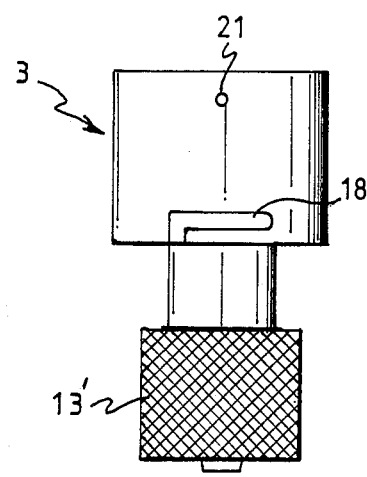
FIG. 8 shows a view of the sleeve with screwed-on head of the sampler of FIGS. 4-6, and FIG. 9, on a larger scale, shows a longitudinal section of the head of FIG. 8.
Figure 9:
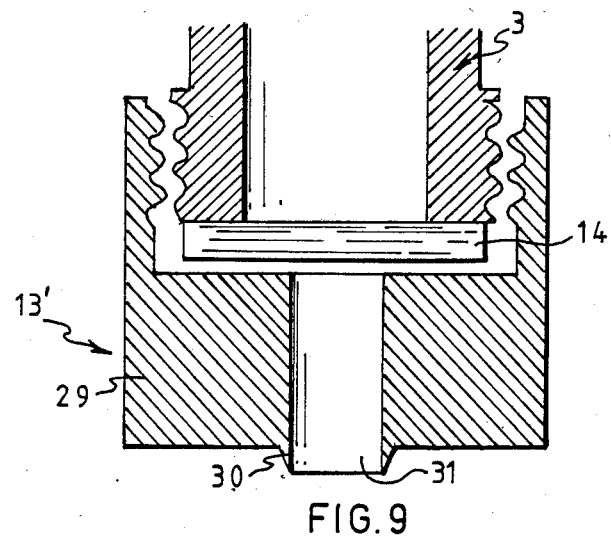

The sampler shown in FIGS. 1-3 substantially comprises four parts, viz. a valve 1, a hood 2, a sleeve 3 and a bottle retainer 4.

The valve 1 is shown extremely schematically and its construction is not essential to the invention. It can be a two- or multi-way valve, dependent on the number of functions that the valve has to perform for the desired processes.

The valve 1 is connected to the hood 2 comprising an axial bore 5 for a proces needle 6 that is to be connected to the interior of the valve, and a relatively wide vent bore 7 in which with the aid of a ring 29 a vent needle has been mounted that is shorter than the process needle, which vent bore 7 debouches, via a perpendicular curve, in a connection 9 for the discharge of air, proces gas or vapour, rinsing medium and/or steam to a receptacle space (not shown).

The bores 5 and 7 extend through a stub 10 projecting in the centre of the hood 1, so that an annular space 11 is formed in which the sleeve 3 can reciprocate.

The sleeve 3 forms in its centre a chamber 12 into which the needles 6 and 8 project. The needles 6 and 8 can also be replaced by a so-called double passage needle.

The end of the sleeve 3 facing away from the valve 1 is reduced in diameter and provided with external screw thread in order to be able to screw on a cap 13 that has a hole, so that said end of the sleeve can be sealed by a septum 14.

With respect to the annular space 11 the chamber 12 has been sealed by a packing 15 that is received in a groove of either the inner wall of the sleeve 3 or the outer wall of the stub 10.

The bottle retainer 4 has such an inner diameter that it can be reciprocated over the hood 2 with clearance. Near the open upper end of the bottle retainer 4 an inwardly directed projection 16 has been mounted which through a specially formed axial slit 17 of the hood 2 (also vide FIG. 2) can project into a slit 18 of the sleeve 3. This slit 18 may have a perpendicular appearance, the substantially horizontal leg extending upwardly along a slight slope.

The bottom of the axial slit 17 is devised as S-curve 19 that partly corresponds with the appearance of the perpendicular slit 18 of the sleeve 3.

Near the upper end of the axial slit 17 there is a branch 20 for receiving the inwardly directed projection 16 of the bottle retainer 4. This arrangement is most effective if the branch 20 is located on the side of the slit 17 that is facing away from the S-curve 19, in view of the sleeve 3 dropping out accidentally.

Through the axial groove 17 an outwardly directed projection 21 of the sleeve 3 can also reciprocate, so that the sleeve will only reciprocate axially.

The bayonet fittings obtained by means of the slits 17 and 18 will fix the bottle retainer 4 both in the lower and in the upper or process position. Although it has not been shown in the drawing, a set of projections or pins 16/21 and pertaining slits 17/18 may have been arranged on the diametrially opposite side.

In principle, the bottle retainer 4 may also have such an outer diameter that it can be reciprocated in the hood 2 with clearance. Because this variant is more complicated since both an inwardly and an outwardly directed pin 16 has to be mounted, the shown embodiment is preferred. It is also conceivable that the bayonet slits are devised unidentical to one another, and that the pins in the sleeve are mounted at different levels, which can also result in a locking.

In order to guarantee that the sleeve 3 is prevented from dropping out of the hood, a countersunk screw 22 may have been screwed through the wall of the hood 2 (FIG. 2), which screw can be received in a nick 23 (FIG. 3) of the sleeve 3.

At the bottom of the bottle retainer 4 a spring 24 is mounted, pushing a septum 26 of a sample bottle 27, mounted by means of a known cap 25, against the septum 14 of the sleeve 3 before the projection 16 can start its axial stroke through the slit 17. The compression of the spring 24 is minimal. If the spring pressure is chosen too great, the sleeve 3 can move upwardly prematurely, and it would become impossible to turn projection 16 into the horizontal portion of the slit 18. The horizontal portion of the slit has sufficient clearance to compensate a slight vertical movement of the sleeve 3. In order to center the sample bottle 27, a set of three ribs 28 may have been arranged at equal angular distances in the bottle retainer 4. If the horizontal portion of the slit 18 extends upwardly somewhat slopingly the spring pressure will increase anyway during upward movement of the sample bottle if such is desired.

The working of the described sampler is as follows: a sample bottle 27, comprising a cap 25 and septum 26, is placed in the bottle retainer 4. The bottle retainer 4 is then slid over the hood 2 from below, the projection 16 arranged in the bottle retainer 4 passing through the slits 17 and 18.

The pin-shaped projection 16, arranged in the bottle retainer 4, also engages the sleeve 3 during its upward sliding movement from below. The upward sliding movement is continued until one or both pins or projections 21 of sleeve 3 have reached the end of the slits 17, after which the bayonet fit is realized by a rotary motion. By sliding the bottle retainer 4 over the hood 2 the needle(s) will have pierced the septum 14 in sleeve 3 and the septum 26 of the sample bottle 27. If now the sample tab is turned into the process position, a sample of sufficient quantity is tapped and then the tap is closed. A checking slit (not shown) may have been arranged in the bottle retainer in the known manner in order to be able to properly observe the filling process in the sample bottle.

If desired and if the valve or valve system is adapted for that purpose, an inert gas can be used for a preliminary rinsing of valve and conduits, c.q. needles.

After the tapping is finished, the sample bottle 27 can be removed. In order to do so the bayonet fit is released and the bottle retainer 4 is removed from the hood 2. The needle(2) 6, 8 is/are not only removed from the septum 26 of the sample bottle 27, but also from the septum 14 of the sleeve 3. The pin 16 projecting into the slit 18 ensures that the sleeve 3 is engaged to slide down when removing the bottle retainer 4 just as it was engaged to slide up when mounting the bottle retainer. The sample bottle can be taken out. In principle, sampling is finished.

In the sleeve 3 there is thus a chamber 12, sealed at the top by the hood 2 and at the bottom by the septum 14, sealing itself, of the sleeve 3. The valve can now be opened again, to admit steam or a rinsing liquid. In case of a two-way valve the valve is put in the process position, with which it is assumed that for the valve 1 there is another option, viz. a multi-way valve or a composition of valves, so as to choose whether the process conduit will supply a process medium or another liquid, air, inert gas or steam. If the valve is a multi-way valve, of which one of the gates is connected to a steam supply, the valve is turned to the "steam position", so that steam flows into the above-stated chamber 12 and is discharged again through he vent needle 8 and connection 9 connected thereto, to a space that will not be defined any further.

The steam flows not only through the needles 6, 8, but also rinses them on the outside. The rest of the chamber 12 is also affected by the steam and entirely brought to steam temperature. This situation is maintained until the space 12 is considered to be free of bacteria, or—in another application—as long as considered necessary. Then the valve 1 is closed again. Any remaining condensate can be blown out by means of an inert gas, if the valve or the installation is equipped for that purpose. The septum 14 can now be removed and replaced by a new one, so that the apparatus is ready for the next sampling action. Replacing the septum can also be performed prior to the next sampling action, if such is desired, c.q. not inconvenient. If required, a special metal cap with grips can be used for continuous steam rinsing, applied instead of the cap 13 with the septum 14 during the period that no sampling is performed.

In the second embodiment as shown in FIGS. 4–9 the same reference numerals have been used as in the first embodiment, in so far as possible. The major difference is found in a screw head 13' that is shown in detail in FIG. 9 and replaces the cap 13 of the first embodiment.

The screw head 13' comprises at its underside a ring 29 with a sharp edge 30 that can form a seal with the septum 26 of the sample bottle 27. The ring 29 defines a small chamber 31 in which the septums 14 and 26 can be desinfected by means of steam or another rinsing medium prior to contacting ambient air. This desinfection is performed in an "intermediate position" shown in FIG. 6 in which the needles 6 and 8 have been withdrawn from the sample bottle but still completely pierce the upper septum 14.

The fact that the screw head 13' is longer in axial direction than the cap 13 affects the appearance of the sleeve 2. According to FIG. 7 the vertical parts of the slits 17 and 18 of the hood are elongated. By projecting the inwardly directed projection 16 of the bottle retainer 4 into the slits 18 and 19 of the sleeve 3 or the hood 2, respectively, and by moving the bottle retainer 4 upwardly up to the vertical end of the slit 19, the sleeve 3 is taken along upwardly until the septum 4 has been pierced. Then the bottle retainer is turned in order to further follow the slit 19. The movement is maintained in the slit 17 of the hood 2 until the projection 21 of the sleeve 3 reaches the end of the slit 17. Then the bottle retainer 4 is turned again, until the projection 16 reaches the end of the horizontal slit of the hood 2. Sampling (FIG. 5) can now be performed. After that the process tap 1 is closed and the bottle retainer is turned back out of the horizontal slit 20 and moved downwardly up to the lower end of the slit 17 (FIG. 6). Now the ends of the needles 6 and 8 an the exposed portion of the septum 26 of the sample bottle 27 can be sterilized.

The pin 21 (FIG. 8) is placed higher than in the first embodiment. Therefore longer needles 6 and 8 have to be chosen.

Other embodiments than the ones shown in the drawing may also fall within the scope of the present invention. In this respect the embodiment in which the bottle retainer can reciprocate in the sleeve is thought of in particular.

I claim:

1. A sampler mechanism for the interconnection of a valve having a plurality of positions and the interior space of a sample bottle having as a closure therefor a resealable septum, said sample mechanism comprising:
   (a) a hood component in mating engagement with said valve at one end of said hood component, and further comprising:
      (i) a first passageway therethrough in fluid communication with said valve at one end thereof, and terminating with a needle tip at the opposite end thereof; and
      (ii) an externally vented second passageway extending for at least a portion of the length of said hood component and terminating with a needle tip at the end of said hood component opposite said valve;
   (b) a sleeve component in mating, reciprocal engagement with said hood component at one end thereof, said sleeve component having a cavity therethrough defining an internal plenum through which the needle tips at the termination of the passageways of said hood component may travel as said hood component and sleeve component reciprocate; and
   (c) a bottle retainer component in mating, reciprocal engagement with said hood component, said bottle retainer component adapted to receive and hold therein a sample bottle with an interior space and having as a closure therefor a resealable septum, for the purpose of sampling,
   and wherein said mechanism is further provided with means to permit reciprocation between an inserted position in which the needle tips of said hood component are inserted through the resealable septum of a sample bottle and penetrate into the interior space of said sample bottle, permitting interconnection and fluid communication between the valve and the interior of said sample bottle, and a withdrawal position in which the needle tips of said hood component are not inserted through the septum and do not penetrate into the interior of said sample bottle and wherein said sleeve component is provided with means for attaching a resealable septum at the end of said cavity opposite said hood component, whereby the needle tips can be rinsed directly before or after sampling.

2. The sampler mechanism of claim 1 wherein the means for attaching a resealable septum comprises a screw cap.

3. The sampler mechanism of claim 2 wherein the screw cap includes a screw head containing the resealable septum and further comprises an interior chamber with an outwardly facing rim to engage the exterior surface of the sample bottle septum.

4. The sample mechanism of claim 3 further provided with means to permit the needle tips to be rinsed directly before or after sampling while the needle tips are in an intermediate position in the anterior chamber of the screw cap.

5. The sampler mechanism of claim 1 further comprising means to seal the upper periphery of the cavity of the sleeve component and the hood component.

6. The sampler mechanism of claim 1 wherein the means to permit reciprocation comprise, at least in part,
   an outwardly directed projection on the sleeve component, and
   an axial slit in the hood component engaging said outwardly directed projection the sleeve component which permits the sleeve to reciprocate only rectilinearly within the hood component.

7. The sampler mechanism of claim 6 further comprising
   an inwardly directed projection on the upward periphery of said bottle retainer component and an angular branch slit intersecting the axial slit to allow the bottle retainer and hood components to be engaged together in a bayonet-type fit by fitting the inwardly directed projection into the branch slit.

8. The sampler mechanism of claim 1 wherein said bottle retainer component further comprises means to hold the septum of a sample bottle in firm engagement with the septum of the sleeve component.

9. The sample mechanism of claim 8 wherein the means to hold the septum of a sample bottle in firm engagement comprises a spring extending between the sample bottle and the bottle retainer component.

10. The sampler mechanism of claim 1 wherein said bottle retainer component further comprises centering means for the proper positioning of a sample bottle.

11. The sample mechanism of claim 10 wherein the centering means comprises at least three inwardly facing ribs.

12. The sampler mechanism of claim 1 wherein said bottle retainer component further comprises means permitting the contents of a sample bottle to be visually checked.

13. The sampler mechanism of claim 1 wherein the needle tip in communication with the valve extends in a direction away from said one end of said hood component further than the externally vented needle tip.

14. The sampler mechanism of claim 1 wherein the externally vented needle tip is affixed with the aid of a ring in a relatively wide vent passageway of the hood component.

* * * * *